(12) United States Patent
Zhao

(10) Patent No.: US 7,754,251 B2
(45) Date of Patent: Jul. 13, 2010

(54) FOOT-BATH AGENT OF CHINESE HERBAL MEDICINE FOR REGULATING BLOOD PRESSURE AND IMPROVING SLEEP QUALITY

(76) Inventor: Guangjun Zhao, 2555 Tuanjie Road, Kuai Da Mao Town, Tong Hua County, Ji Lin Province 132000 (CN)

( * ) Notice: Subject to any disclaimer, the term of this patent is extended or adjusted under 35 U.S.C. 154(b) by 0 days.

(21) Appl. No.: 12/208,335

(22) Filed: Sep. 11, 2008

(65) Prior Publication Data

US 2009/0269423 A1 Oct. 29, 2009

(30) Foreign Application Priority Data

Apr. 23, 2008 (CN) .................. 2008 1 0011151

(51) Int. Cl.
*A61K 36/00* (2006.01)
*A61K 9/00* (2006.01)
*A61K 31/00* (2006.01)

(52) U.S. Cl. ............................. 424/725; 424/400; 514/1

(58) Field of Classification Search ........................ None
See application file for complete search history.

(56) References Cited

FOREIGN PATENT DOCUMENTS

| CA | 2385271 A1 | * | 11/2003 |
| CN | 1123610 A | * | 6/1996 |
| CN | 1907406 A | * | 2/2007 |
| CN | 101015653 A | * | 8/2007 |

OTHER PUBLICATIONS

Treatment Modalities: Herbal foot baths to promote health. Internet Archive Date: May 19, 2007 [Retrieved from the Internet on: Jun. 19, 2009]. Retrieved from: <http://web.archive.org/web/20070519155702/http:/www.shen-nong.com/eng/treatment/footbaths.html>.*

* cited by examiner

*Primary Examiner*—Amy L Clark
(74) *Attorney, Agent, or Firm*—Yi Li

(57) ABSTRACT

The present invention relates to a foot-bath agent for regulating blood pressure and improving sleep quality, which includes fructus leonuri 20-25%, semen ziziphi spinosae 15-20%, calcined magnetitum 17-22%, spica prunellae 15-20%, ligusticum chuanxiong hort 18-23%, and borneolum 0.7-1.2% by weight. The foot-bath agent has advantages including no allergy and less side effects to human body.

1 Claim, No Drawings

FOOT-BATH AGENT OF CHINESE HERBAL MEDICINE FOR REGULATING BLOOD PRESSURE AND IMPROVING SLEEP QUALITY

TECHNICAL FIELD

The invention relates to a foot-bath agent of Chinese herbal medicine for regulating blood pressure and improving sleep quality.

RELATED ART

Hypertension is a multifactorial disease which is caused by interactions among some genetic genes, many pathogenic factors for blood pressure elevation and physiological factors, of which insomnia is a major clinical symptom.

The prior methods for treating the above disease mainly control the disease by orally administering drugs for lifelong treatment. Such prior treatment methods have disadvantages of more side effects, recurrence after drug withdrawal and high price due to the characteristics of the drugs themselves, though these methods may have therapeutic effects which have been accepted conventionally.

SUMMARY

An object of the invention is to provide a foot-bath agent of Chinese herbal medicine for treating hypertension and improving sleep quality produced by using natural Chinese herbal medicines which have the functions of "promoting blood circulation, regulating menstruation, suppressing yang, receiving qi, tranquilizing mind", via physical method, in accordance with the human body meridian theory in Traditional Chinese Medicine. The effects of regulating blood pressure and improving sleep quality can be obtained by dissolving the foot bath agent prepared according to the invention in hot water at a conventional temperature for foot bathing, and then bathing feet in said hot water containing the dissolved agent.

The components of the formula of the invention are as follows:

fructus leonuri 20-25%, semen ziziphi spinosae 15-20%, calcined magnetitum 17-22%, spica prunellae 15-20%, ligusticum chuanxiong hort 18-23%, borneolum 0.7-1.2%, Provided that, after the final product is prepared using the above raw materials and the blending ratios thereof, the sum of all components should be 100% by weight.

The manufacturing method of the invention is as follows: fructus leonuri 20-25%, semen ziziphi spinosae 15-20%, calcined magnetitum 17-22%, spica prunellae 15-20%, ligusticum chuanxiong hort 18-23% and borneolum 0.7-1.2% were crushed into 100-300 mesh fine powder, mixed homogeneously, sterilized with cobalt 60 for 10 to 24 hours and then packaged separately.

When comparing the method for treating the hypertension and insomnia in sanitary way by bathing feet in the hot water containing said dissolved agent with the prior method for treating the hypertension and insomnia by orally administering drugs, a conclusion can be drawn based on adequate cases and clinical data that the foot bath agent prepared by the invention has advantages including an efficacious and healthy method thereof being highly consistent with healthy living habits of people, an effective regulation of blood pressure and improvement of sleep quality, no allergy and less side effects to human body, and thus obviously is worthy to be popularized and has market prospect.

MODE OF CARRYING OUT THE INVENTION

The invention will be further described by way of an example.

The components of the formula in the Example of the invention are as follows:

fructus leonuri 235 g, semen ziziphi spinosae 175 g, calcined magnetitum 200 g, spica prunellae 175 g, ligusticum chuanxiong hort 205 g, borneolum 10 g.

The manufacturing method in the Example of the invention is as follows: the components of the formula in the Example including fructus leonuri, semen ziziphi spinosae, calcined magnetitum, spica prunellae, ligusticum chuanxiong hort and borneolum were crushed into 120 mesh fine powder, sieved, mixed homogeneously, sterilized with cobalt 60 for 12 hours and then packaged in the form of 20 g per pack.

I claim:

1. A foot-bath agent for regulating blood pressure and improving sleep quality comprising:
   20-25% by weight of Fructus Leonuri,
   15-20% by weight of Semen Ziziphi Spinosae,
   17-22% by weight of calcined magnetitum,
   15-20% by weight of Spica Prunellae,
   18-23% by weight of Ligusticum chuanxiong Hort, and
   0.7-1.2% by weight of borneolum,
   wherein said agent is in the form of a mixed fine powder.

* * * * *